(12) United States Patent
Wang et al.

(10) Patent No.: US 9,605,305 B2
(45) Date of Patent: Mar. 28, 2017

(54) METHOD FOR REDUCING PRIMER-DIMER AMPLIFICATION

(71) Applicant: PILLAR BIOSCIENCES INC., Natick, MA (US)

(72) Inventors: Zhaohui Wang, Southborough, MA (US); Gang Song, Newton, MA (US)

(73) Assignee: PILLAR BIOSCIENCES INC., Natick, MA (US)

( * ) Notice: Subject to any disclaimer, the term of this patent is extended or adjusted under 35 U.S.C. 154(b) by 0 days.

(21) Appl. No.: 15/184,014

(22) Filed: Jun. 16, 2016

(65) Prior Publication Data

US 2017/0009281 A1    Jan. 12, 2017

Related U.S. Application Data

(60) Provisional application No. 62/189,686, filed on Jul. 7, 2015.

(51) Int. Cl.
  *C12Q 1/68*   (2006.01)
  *C07H 21/02*  (2006.01)

(52) U.S. Cl.
  CPC ......... *C12Q 1/6848* (2013.01); *C12Q 1/6853* (2013.01)

(58) Field of Classification Search
  CPC .............. C12Q 1/686; C12Q 2563/179; C12Q 2525/155; C12Q 1/6874; C12Q 2563/131; C12Q 2525/161; C12Q 2525/313; C12Q 2527/143; C12Q 2531/113; C12Q 2535/122; C12Q 2549/119; C12Q 2565/518; C12Q 2565/629; C12Q 1/6806
  See application file for complete search history.

(56) References Cited

U.S. PATENT DOCUMENTS

| 6,207,372 | B1 | 3/2001 | Shuber |
| 8,318,434 | B2 | 11/2012 | Cuppens |
| 2010/0273219 | A1 | 10/2010 | May et al. |
| 2010/0285537 | A1 | 11/2010 | Zimmermann |
| 2011/0287510 | A1 | 11/2011 | Nelson et al. |
| 2013/0005585 | A1 | 1/2013 | Anderson et al. |

FOREIGN PATENT DOCUMENTS

| WO | 2004/016811 A2 | 2/2004 |
| WO | 2011/046972 A2 | 4/2011 |
| WO | 2015/026873 A1 | 2/2015 |

OTHER PUBLICATIONS

Shuber, A.P. et al., Genome Res., vol. 5, pp. 488-493 (1995).*
Grunenwald, H., Meth. Mol. Biol., vol. 226, pp. 89-99 (2003).*
(Continued)

*Primary Examiner* — Teresa Strzelecka
(74) *Attorney, Agent, or Firm* — Perkins Coie LLP; Viola T. Kung

(57) ABSTRACT

The present invention reduces primer-dimer amplification in a multiplex polymerase chain reaction (PCR). When a first forward primer (F1) and a second reverse primer (R2) have a complementary region at their 3'ends, primer dimers may form. The present method uses a primer comprising a 5'-end partial sequence or a full sequence of a first forward primer (F1^) in between a first tag (t1) and R2 to reduce the primer-dimer (F1_R2) amplification.

11 Claims, 4 Drawing Sheets

(56) References Cited

OTHER PUBLICATIONS

International Search Report and Written Opinion dated Sep. 14, 2016 in PCT/US16/37918.
Mamanova et al., "Target-enrichment strategies for next-generation sequencing," Nature Methods, vol. 7, No. 2, Feb. 2010, pp. 111-118.
Mertes et al., "Targeted enrichment of genomic DNA regions for next-generation sequencing," Briefings in Functional Genomics, Downloaded from http://bfgp.oxfordjournals.org/by guest on Jan. 27, 2015, pp. 1-13.
Wen et al., "Universal Multiplex PCR: a novel method of simultaneous amplification of multiple DNA fragments," Plant Methods, 2012, vol. 8:32, pp. 1-9.
Brownie et al., "The elimination of primer-dimer accumulation in PCR", Nucleic Acids Res, Aug. 15, 1997, vol. 25, No. 16, pp. 3235-3241.

* cited by examiner

5' caacgatcgtcgaattcgCAAAATGATGAAGTGACAGTTCCAG 3'    t1-F1
                           ||||||||
               t1-R2  3'  CAAGGTCATGATTACTTCACCCGAcgcttaaagctgctagcaac 5'

FIG. 2

METHOD FOR REDUCING PRIMER-DIMER AMPLIFICATION

This application claims priority to U.S. Provisional Application No. 62/189,686, filed Jul. 7, 2015; the contents of which is incorporated herein by reference in its entirety.

TECHNICAL FIELD

The present invention relates to a method for reducing primer-dimer amplification in a multiplex polymerase chain reaction (PCR).

BACKGROUND OF THE INVENTION

Multiplex-PCR consists of multiple primer sets within a single PCR mixture to produce amplicons that are specific to different DNA sequences. By targeting multiple genes at once, additional information may be gained from a single test run that otherwise would require several times the reagents and efforts to perform.

One of the major obstacles that can decrease the assay sensitivity of multiplex-PCR is the accumulation of primer-dimers (PD). A PD consists of primer molecules that hybridize to each other due to strings of complementary bases, particularly at the 3'-ends of the primers. The presence of many primer pairs at very high concentrations in multiplex PCR reactions increases the chances of formation of primer dimers. Once formed, short PD tend to be amplified very efficiently, potentially inhibiting the amplification of the desired DNA sequences by the massive consumption of primers and other reagents. PD formation can be reduced by a combination of different approaches, including special primer design and modification methods, the use of hot start Taq polymerase, PCR additives and optimized PCR cycling conditions.

Various primer design and modification methods have been reported to reduce the PD formation. Brownie et al (Nucleic Acids Res, 25(16): 3235-41, 1997) describe HANDS (Homo-Tag Assisted Non-Dimer System). In HANDS PCR, all target-specific primers contain a common tail sequence at their 5' ends at low concentration and are mixed with a single tail-specific primer at a higher concentration. After at least two cycles of target specific PCR, the annealing temperature is elevated for the subsequent amplification cycles which are driven entirely by the tail-specific primer. Consequently, the single strands from all PCR products, including desired amplicons and side-products such as PD, have complementary 5' and 3' ends leading to the formation of the same stem-loop structures. Due to the high local concentrations of the tail sequences, the stem-loop structures formed in short products, such as PD, are very stable and out-compete the subsequent annealing of the tail-specific primer, resulting in the inhibition of PD amplification. However, with the same tail sequence on each end of all primers, this method requires the targeted amplicons to be long enough to minimize the inhibitory effects of stem loops on the real target products. Depending on the length and the composition of targeted amplicons in a highly multiplexed PCR, the tightness of the stem loop of each amplicon varies, which may lead to significantly imbalanced amplification. Furthermore, the stem loop may not be stable enough to inhibit PD formation between long primers.

U.S. Pat. No. 5,792,607 (Backman et al) and U.S. Patent Application Publication No. 20140329245 disclose a method using endonuclease IV to cleave off the modified non-Extendable 3' of the primers to activate the primers upon specific primer-template hybridization. Dobosy et al. (BMC Biotechnol. 11: 80, 2011) report a rnase H-dependent PCR (rhpcr) Method using rnase H to cleave off a single RNA base positioned close to the 3'-end of the Blocked primers to activate the primers upon the primer-template specific hybridization. This Method was commercialized recently by IDT (Integrated DNA Technologies, US Patent Application Publication No. 2009/0325169, PCT/US2012/030413). All of these approaches require modified bases in primers and additional enzymes for primer activation, which results in higher cost.

Peleg et al (Appl. Environ. Microbiol., 75: 6393-6398, 2009; WO/2009/004630) report that DNA-RNA chimeric primers in PCR reduces PD formation. Dual Priming Oligonucleotide (DPO) primer (Seegene Technologies) has been reported to reduce PCR PD formation (Chun et al., Nucleic Acids Res. 35(6): e40, 2007). DPO comprises of two separate priming regions (5'-end stabilizer and 3'-end determiner) joined by a polydeoxyinosine linker. Non-specific hybridizations of the primers, such as PD, are reduced at the 3'-end of the DPO primer due to the "bubble"-like structure comprised of the weak hydrogen bonds of the polydeoxyinosine linker. The above RNA bases in the chimeric primers and the polydeoxyinosine linker in the DPO primers significantly increase the complexity and the cost of primer manufacturing.

Scatterfield (J. Mol. Diagn., 16: 163-173, 2013) reports cooperative primers that consist of two DNA sequences linked through a polyethylene glycol linker either 5' to 5' or 5' to 3'. The results indicate that singleplex PCR reactions using cooperative primers greatly reduce primer-primer propagation in the presence of added primer dimers.

Despite these efforts, PD formation remains a big challenge in multiplex PCR. In particular, the multiplex level for target enrichment in next generation sequencing (NGS) applications is extremely high when hundreds of or even thousands of primers are present in the same PCR reaction pool. All of these primers can potentially form primer dimers.

BRIEF DESCRIPTION OF THE DRAWING

FIG. 2 shows that F1 and R2 have 7 complimentary bases at their 3'-ends and form a primer dimer. t1-F1 and t1-R2 are identified as SEQ ID NOs: 7 and 9, respectively.

DETAILED DESCRIPTION OF THE INVENTION

Definition

Figure 1A:
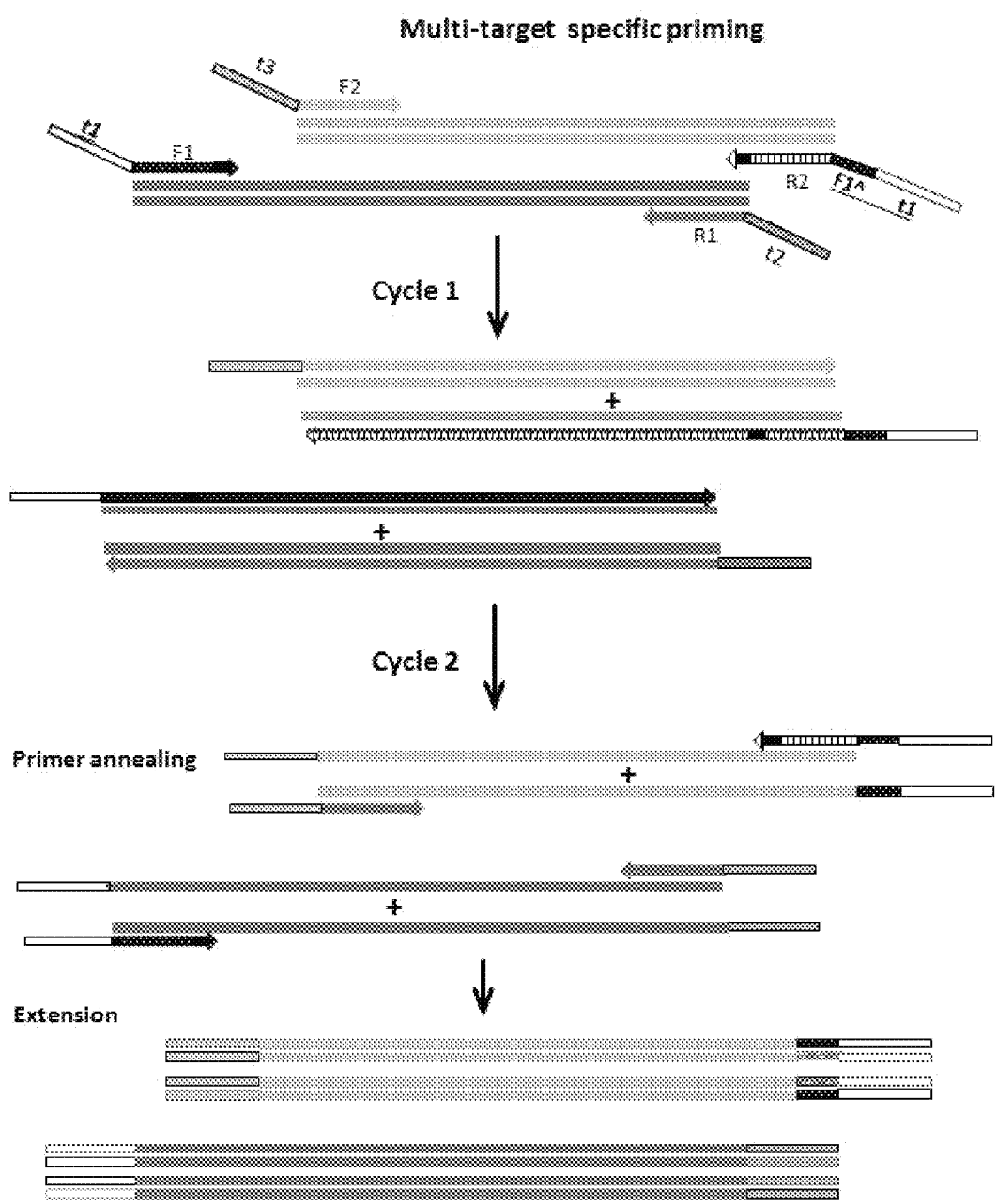
FIG. 1A illustrates a first cycle and a second cycle of PCR for amplification of two target sequences, with t1F1, t2R1, t3F2, and t1F1 ^R2 as primers.

An "amplicon" is a piece of DNA or RNA that is the source and/or product of natural or artificial amplification or replication events. In this context, "amplification" refers to the production of one or more copies of a genetic fragment or target sequence, specifically the amplicon. As the product of an amplification reaction, amplicon is used interchangeably with common laboratory terms, such as PCR product.

A "primer dimer" (PD) is a potential by-product in PCR. A PD consists of primer molecules that are hybridized to each other because of complementary bases in the primers.

The present invention is directed to a method for reducing primer-dimer amplification in a multiplex polymerase chain reaction (PCR). When a first forward primer (F1) and a second reverse primer (R2) have a complementary region at their 3' ends, primer dimer formation may occur. Due to the high concentrations of primers, the complementary region may be as short as 2-3 nucleotides to cause primer dimer amplification. When the complementary region is at least 4 or 5 nucleotides, the undesired primer dimer amplification is almost certain to occur.

The present method reduces the primer dimer problem when a first forward primer (F1) and a second reverse primer (R2) have a complementary region at their 3'ends. The method comprises the steps of: (a) obtaining a first nucleic acid sequence comprising a first tag (t1) and a first forward primer (F1) complementary to a first target nucleic acid fragment, (b) obtaining a second nucleic acid sequence comprising a second tag (t2) and a first reverse primer (R1) complementary to the first target nucleic acid fragment, (c) obtaining a third nucleic acid sequence comprising a third tag (t3) and a second forward primer (F2) complementary to a second target nucleic acid fragment, (d) obtaining a fourth nucleic acid sequence comprising the first tag (t1), a second reverse primer (R2) complementary to the second nucleic acid fragment, and a 5'-end partial sequence (F1^) or a full sequence of the first forward primer in between the first tag (t1) and the second reverse primer (R2), (e) mixing the first and the second target nucleic acid fragments, the first, the second, the third, and the forth nucleic acid sequences, and an effective amount of reagents necessary for performing a polymerase chain reaction (PCR); and (f) performing PCR.

F1, R1, F2, R2 are gene-specific primers, which are complementary to specific regions of genomic DNA (target DNAs or amplicons). The length of these primers can be chosen by a person skilled in the art. In general, the gene-specific primers are 6-40, 10-50, or 10-100 nucleotides in length. For example, the gene-specific primers can be 15-30 nucleotides.

F1^ is the 5' portion of the F1 primer sequences that are tagged at the 5'-end of the R2 primer; F1^ can be a full sequence or partial sequence of F1. The length of F1^ may depend on its GC content, which affects its melting point when it hybridizes to complementary bases. In one embodiment, the partial sequence of F1^ is 1-20, 1-10, or 1-5 nucleotides shorter than F1. In one embodiment, the partial sequence of F1^ contains 10-50, 20-80, 30-70, 40-90, or 50-90% of the F1 sequence. In another embodiment, the partial sequence of F1^ contains 3-30, or 5-20, or 8-15 nucleotides.

Tags t1, t2, and t3 are universal tag sequences that do not bind to the target DNAs. In one embodiment, tags t2 and t3 have identical sequences. In another embodiment, t2 and t3 are different, i.e., they are not 100% identical. Both tags t2 and t3 are different from tag t1. Each tag is at the 5' end of a gene-specific primer. In the present invention, the tag sequences are at least 3 nucleotides in length, and can be 5-100, 3-40, or 10-30 nucleotides long. Tags typically are designed to add at least 5° C. to the melting temperature of the gene-specific untagged primers. Tag sequences can be modified or unmodified nucleic acids. Many modified bases (e.g. locked nucleic acids or peptide nucleic acids) have higher annealing temperatures than their corresponding natural bases. When shorter tag sequences are desired for various reasons, those modified bases can be used instead of the natural bases.

Figure 1B:
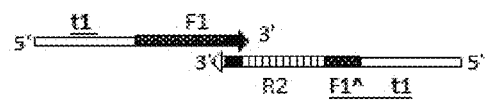
FIG. 1B illustrates the interaction of F1 and R2, and the formation, amplification, and inhibition of primer dimer.
Figure 1B:
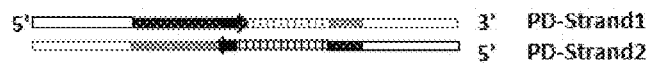
Figure 1B:
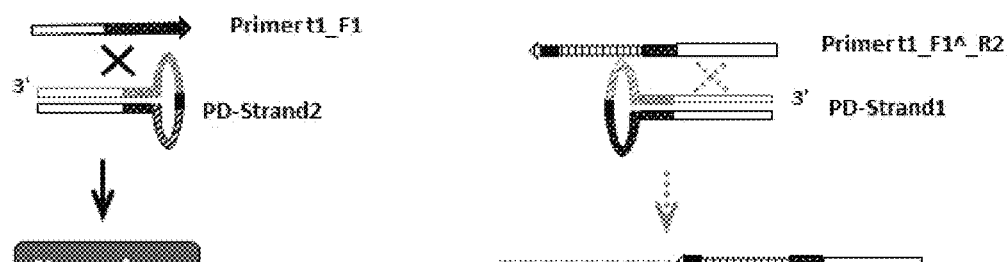

FIGS. 1A and 1B are used for illustration purpose and the present invention is not meant to be limited to the drawings only. FIG. 1A shows a typical PCR amplification with two target sequences that have no overlapping regions. FIG. 1B shows PD formation by F1 and R2 primers and inhibition of the PD accumulation by the stem-loop structure.

FIG. 1B illustrates how the present invention prevents the exponential amplification of a primer dimer. In FIG. 1B, a forward primer F1 and a reverse primer R2 have a complementary region at their 3'-ends. After Cycle 1, PD-Strand 1 and PD-Strand 2 are formed. In Cycle 2, on the left side, PD strand 2 forms a stem loop, in which t1 and F1^ anneal to their complementary counterparts respectively to form a stem, and the remaining nucleotides form a loop. Due to high local concentrations of t1 and F1^ and their respective complementary counterparts, i.e., they are on the same PD Strand 2 and are close to each other, the formation of the stem loop is more favorable than the annealing with a separate t1F1 primer; therefore, further primer annealing is blocked, and no further amplification product of PD-Strand 2 can be obtained. The presence of F1^ is important in order to completely block the primer (t1_F1) annealing to PD Strand 2 and then the amplification of PD Strand 2. Without F1^, the primer t1_F1 may outcompete the stem structure containing only t1 and then anneal to PD Strand 2. With the addition of F1^, primer t1_F1 can no longer outcompete the stem structure containing t1_F1 ^ for annealing to PD Strand 2.

In Cycle 2 of FIG. 1B, on the right side, similar to PD Strand 2, PD strand 1 also forms a stem loop, in which t1 and F1^ anneal to their complementary counterparts respectively to form a stem, and the remaining nucleotides form a loop. Because of the longer length and thus higher melting point of tagged R2 primer (t1_F1^_R2), this primer may outcompete the t1_F1^ in the stem for annealing, and possible linear amplification may be obtained for PD Strand 1. FIG. 1B illustrates the invention that with the primer design of t1F1 and t1_F1^R2, PD would at most be amplified linearly for one strand, and would not be amplified exponentially.

In step (f) of the present method, the PCR can be performed as one stage (one cycling condition) or two stages (two different cycling conditions). In two-stage PCR, the annealing temperature is increased in the second cycling condition, which further reduces the primer dimer formation.

In one-stage, the PCR comprises the steps of: (f1) activating DNA polymerase and denaturing DNAs in the mixture of (e), and (f2) cycling the mixture of (f1) through denaturing, annealing and primer extension steps of PCR multiple times to obtain amplification products.

In two-stage, the PCR comprises the steps of: (f-i) activating DNA polymerase and denaturing DNAs in the mixture of (e), (f-ii) cycling the mixture of (f-i) through denaturing, annealing and primer extension steps of PCR at least two times, and (f-iii) cycling the mixture of (f-i) through denaturing, annealing and primer extension steps of PCR at an annealing temperature higher than that in step (f-ii) to obtain amplification products.

In two-stage PCR, in step (f-ii), the mixture of nucleic acids and reagents goes through the PCR cycle of denaturing, annealing and primer extension steps at least two times, such as 2-5 times. In step (f-iii), the mixture of (f) goes through more cycles of PCR of denaturing, annealing and primer extension; this time at an annealing temperature higher than that in step (f-ii). For example, the annealing temperature in step (f-iii) is about 4-35° C., or 5-25° C., or 6-20° C., or 6-15° C. higher than the annealing temperature in step (f-ii). For example, the first temperature of the first cycles of annealing and extension (step f-ii) is 58-62° C., e.g., 60° C., and the second temperature of the second cycles of annealing and extension (step f-iii) is 66-70° C., e.g., 68° C.

In two-stage PCR, the annealing temperature in the second stage (f-iii) is increased to prevent the repeated initiation of primer-dimer. After the first stage of PCR (f-ii), each amplified target sequence product is lengthened by the tags at both ends and accordingly the annealing regions are lengthened by the tags. Therefore, increasing annealing temperatures in the second stage will not affect the primer annealing to specific target DNAs. However, increasing annealing temperatures in the second stage will reduce the primer dimer initiation, in which the complementary regions remain the same length.

The following examples further illustrate the present invention. These examples are intended merely to be illustrative of the present invention and are not to be construed as being limiting.

EXAMPLES

Table 1 shows oligonucleotide sequences used in the following examples.

Oligo 1-4 in Table 1 are target specific primers for BRCA1 gene Amplicon1 and Amplicon2 without the tag sequences; Amplicon 1 and Amplicon 2 do not have overlapping sequences. Oligo 5-6 are tag sequences from Illumina TSCA tag-sequences. Oligo 7-15 are the tagged primers used in Examples 1-3.

F1 and R2 have 7 complimentary bases at their 3'-ends and form a heterodimer as shown in FIG. 2.

Table 2 shows the amplicon sizes including PD, and locations on human genome 19.

TABLE 2

| Amplicon Name | Gene | Chr hg19 | Start hg19 | End hg19 | Size Gene Specific (bp) | Size With Tag (bp)* |
|---|---|---|---|---|---|---|
| Amplicon1 (A1) | BRCA1 | chr17 | 41199461 | 41199792 | 332 | 373 |
| Amplicon2 (A2) | BRCA1 | chr17 | 41244382 | 41244637 | 256 | 297 |
| F1 + R2 Dimer | N/A | N/A | N/A | N/A | 41 | 81 |

*Sizes only reflect the amplicons using primers that are tagged with t1 and t2 without F1

Table 3 shows information for the primer combinations in Examples 1, 2 and 3.

TABLE 1

| SEQ ID NO: | | Sequence* | Direction Size(nt) | Amplico |
|---|---|---|---|---|
| 1: | F1 | AAAATGATGAAGTGACAGTTCCAG | FWD 24 | Amplicon 1 |
| 2: | R1 | CCCATGGAAACAGTTCATGTATTA | REV 24 | Amplicon 1 |
| 3: | F2 | CATGGACTTTTACAAAACCCATATC | FWD 25 | Amplicon 2 |
| 4: | R2 | AGCCCACTTCATTAGTACTGGAAC | REV 24 | Amplicon 2 |
| 5: | t1 | caacgatcgtcgaaattcgc | 20 | NR |
| 6: | t2 | tacacgacgctcttccgatct | 21 | NR |
| 7: | t1_F1 | caacgatcgtcgaaattcgc AAAATGATGAAGTGACAGTTCCAG | FWD 44 | Amplicon 1 |
| 8: | t2_R1 | atcacgacgctcttccgatct CCCATGGAAACAGTTCATGTATTA | REV 45 | Amplicon 1 |
| 9: | t1_F1^0_R2 | caacgatcgtcgaaattcgc AGCCCACTTCATTAGTACTGGAAC | REV 44 | Amplicon 2 |
| 10: | t1_F1^3_R2 | caacgatcgtcgaaattcgc <u>AAA</u> AGCCCACTTCATTAGTACTGGAAC | REV 47 | Amplicon 2 |
| 11: | t1_F1^6_R2 | caacgatcgtcgaaattcgc <u>AAAATG</u> AGCCCACTTCATTAGTACTGGAAC | REV 50 | Amplicon 2 |
| 12: | t1_F1^9_R2 | caacgatcgtcgaaattcgc <u>AAAATGATG</u> AGCCCACTTCATTAGTACTGGAAC | REV 53 | Amplicon 2 |
| 13: | t1_F1^12_R2 | caacgatcgtcgaaattcgc <u>AAAATGATGAAG</u> AGCCCACTTCATTAGTACTGGAAC | REV 56 | Amplicon 2 |
| 14: | t1_F1^15_R2 | caacgatcgtcgaaattcgc <u>AAAATGATGAAGTGA</u> AGCCCACTTCATTAGTACTGGAAC | REV 59 | Amplicon 2 |
| 15: | t2_F2 | tacacgacgctcttccgatct CATGGACTTTTACAAAACCCATATC | FWD 46 | Amplicon 2 |

*Lower case indicates tag sequences; Underline indicates inserted partial F1 sequences in R2; Unlabeled upper case sequences are gene-specific sequences

TABLE 3

| Lane ID | Name | PCR primer mix* Amplicon1 (A1) | | Amplicon2 (A2) | | F1_R2 Dimer Stem components; size Stem (nt) |
|---|---|---|---|---|---|---|
| 1 | 1-plex A1 | t1_F1 | t2_R1 | | | Not relevant |
| 2 | 1-plex A2 | | | t2_F2 | t1_F1^0_R2 | |
| 3 | 2-plex | t1_F1 | t2_R1 | t2_F2 | t1_F1^0_R2 | t1_only; –20 |
| 4 | | t1_F1 | t2_R1 | t2_F2 | t1_F1^3_R2 | t1_F1^3; –23 |
| M | | | | 50 bp Ladder | | |
| 5 | 2-plex | t1_F1 | t2_R1 | t2_F2 | t1_F1^6_R2 | t1_F1^6; –26 |
| 6 | | t1_F1 | t2_R1 | t2_F2 | t1_F1^9_R2 | t1_F1^9; –29 |
| 7 | | t1_F1 | t2_R1 | t2_F2 | t1_F1^12_R2 | t1_F1^12; 32 |
| 8 | | t1_F1 | t2_R1 | t2_F2 | t1_F1^15_R2 | t1_F1^15; 36 |

*The interacting primers, which contains F1 and R2, are shown in bold in the 2-plex PCR primer mix

Example 1: 1-Stage PCR Amplification

A typical 25 μL PCR reaction mixture of gene-specific PCR included: 2 μL of human genomic DNA (Promega Cat# G3041, diluted to 5 ng/μL using Low TE buffer (USB Cat#75793)), 12.5 μL of 2× Master Mix (Qiagen Cat#206413), 8.5 μL nuclease-free water, and 2 μL of gene-specific primer mix (2.5 μM each, see Table 3 for mixing information and Table 1 for oligonucleotide sequences).

Both 1-plex and 2-plex PCR reactions were performed on a thermal cycler as follows:

| 1 Cycle | 95° C. | 15 min Enzyme activation and initial DNA denaturation |
|---|---|---|
| 30 Cycles | 95° C. | 30 sec Denaturation |
| | 60° C. | 90 sec Annealing/extension |
| 1 Cycle | 72° C. | 5 min Final extension |
| 1 Cycle | 8° C. | Hold |

In this example, the annealing and extension temperature remained constant during the cycling; therefore, it was referred as 1-stage PCR amplification.

Example 2: 2-Stage PCR Amplification

Similar PCR reaction mixes were used as in Example 1 but with a 2-stage PCR cycling protocol on a thermal cycler. The first five cycles of annealing and extension were performed at 60° C., the same temperature used in Example 1; the subsequent 25 cycles of annealing and extension were performed at an increased temperature of 68° C. to inhibit the initiation of primer dimers.

The 2-stage PCR protocol is listed as follows:

| 1 Cycle | 95° C. | 15 min Enzyme activation and initial DNA denaturation |
|---|---|---|
| 5 Cycles | 95° C. | 30 sec Denaturation |
| | 60° C. | 90 sec Annealing/extension |
| 25 Cycles | 95° C. | 30 sec Denaturation |
| | 68° C. | 90 sec Annealing/extension at an increased temperature |
| 1 Cycle | 72° C. | 5 min Final extension |
| 1 Cycle | 8° C. | Hold |

Example 3: Agarose Gel Electrophoresis

PCR products were analyzed on an E-Base device (Life Technologies). 2 μL of each PCR product was mixed with 18 μL nuclease-free water and then directly loaded onto a 2% E-gel. DNA electrophoresis of diluted PCR products and 50 bp DNA Ladder (Invitrogen Cat#10488-043) was performed. At the end of the run, a digital image of the gel was captured by an E-gel Imager (Life Technologies). The results are shown in FIG. 3.

Figure 3:
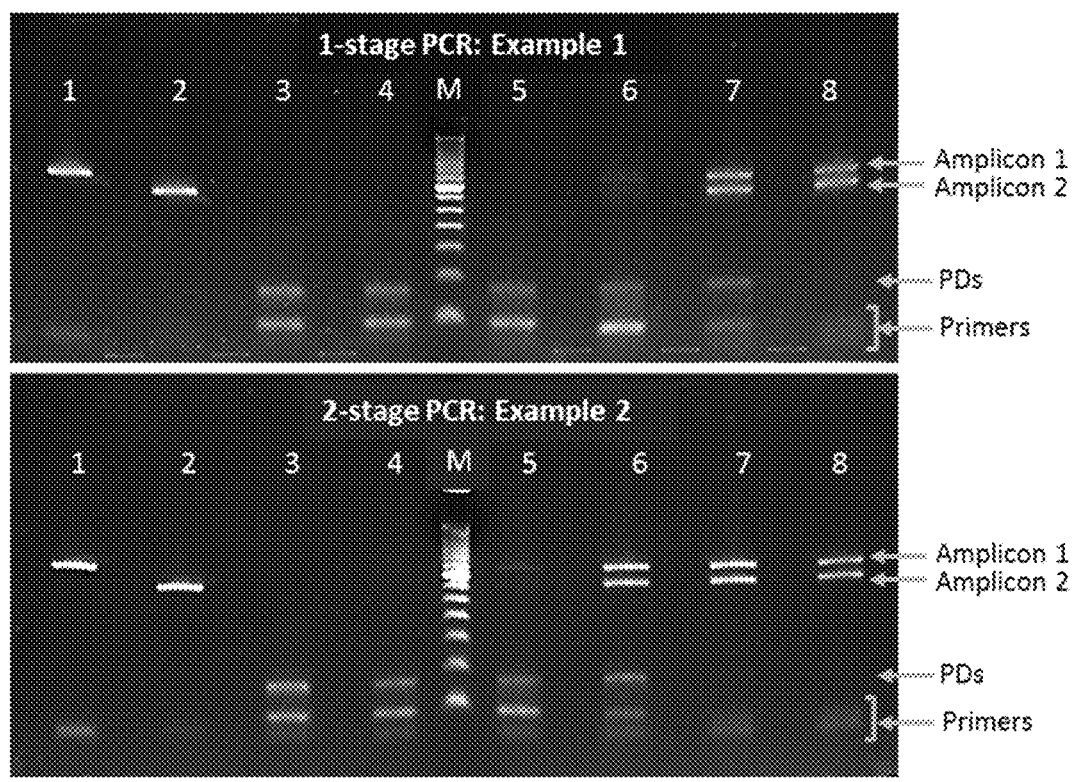
FIG. 3 shows the results of gel electrophoresis of PCR products by 1-stage PCR amplification (top panel) and 2-stage PCR amplification (bottom panel). Lane 1: 1-plex amplicon 1, Lane 2: 1-plex amplicon 2, Lanes 3-8: 2-plex with primer t1_F1^x_R2, where x=0, 3, 6, 9, 12, 15 nucleotides, respectively. Lane M: 50 base DNA Ladder.

In FIG. 3, the top panel shows the results from the 1-stage PCR protocol (Example 1) and the bottom panel shows the results from the 2-stage PCR protocol (Example 2). Lanes 1 and 2 are 1-plex PCR showing the sizes of targeted Amplicons 1 and 2. The remaining reactions are all 2-plex PCR (Lanes 3-8). When these two amplicons were multiplexed together, due to the strong interaction of the 3'-ends of F1 and R2, the F1+R2 dimer amplicons were formed and dominated the PCR reaction (as shown in Lanes 3) under both 1-stage and 2-stage PCR conditions. The stem structures formed in the PD in Lanes 4-8 contains t1 sequences (20 nt) in addition to 3, 6, 9, 12 and 15 nucleotides of the 5'-end part of F1 sequences respectively. Introducing partial F1 sequences reduced the dimer amount detected in Lanes 4-8 comparing with Lane 3 (no F1 sequence). When the dimer amplifications were sufficiently inhibited, the targeted amplicons became detectable (Lane 6 in the upper panel and Lane 5 in the lower panel). When nearly complete inhibition of the dimer amplifications was reached in Lane 7-8 in both panels, the two products of the targeted amplicons dominated the reactions.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method for reducing primer-dimer amplification in a multiplex polymerase chain reaction (PCR), comprising the steps of:
   (a) obtaining a first nucleic acid sequence comprising a first tag (t1) and a first forward primer (F1) complementary to a first target nucleic acid fragment,
   (b) obtaining a second nucleic acid sequence comprising a second tag (t2) and a first reverse primer (R1) complementary to the first target nucleic acid fragment,
   (c) obtaining a third nucleic acid sequence comprising a third tag (t3) and a second forward primer (F2) complementary to a second target nucleic acid fragment,
   (d) obtaining a fourth nucleic acid sequence comprising the first tag (t1), a second reverse primer (R2) complementary to the second nucleic acid fragment, and a 5'-end partial sequence (F1^) or a full sequence of the first forward primer (F1) in between the first tag (t1) and the second reverse primer (R2), wherein the first forward primer (F1) and the second reverse primer (R2) have a complementary region at their 3'ends, F1^ has 3-30 nucleotides or 40-90% of the 5'-end partial F1 sequence,
   (e) mixing the first and the second target nucleic acid fragments, the first, the second, the third, and the fourth nucleic acid sequences, and an effective amount of reagents necessary for performing a polymerase chain reaction (PCR); and
   (f) performing PCR.

2. The method according to claim 1, wherein step (f) comprises:
   (f1) activating DNA polymerase and denaturing DNAs in the mixture of (e),
   (f2) cycling the mixture of (f1) through denaturing, annealing and primer extension steps of PCR multiple times to obtain amplification products.

3. The method according to claim 1, wherein step (f) comprises:
   (f-i) activating DNA polymerase and denaturing DNAs in the mixture of (e),
   (f-ii) cycling the mixture of (f-i) through denaturing, annealing and primer extension steps of PCR at least two times, and
   (f-iii) cycling the mixture of (f-ii) through denaturing, annealing and primer extension steps of PCR multiple times at an annealing temperature higher than that in step (f-ii) to obtain amplification products.

4. The method according to claim 3, wherein the annealing temperature in step (f-iii) is 4-35° C. higher than the annealing temperature in step (f-ii).

5. The method according to claim 1, wherein tags t3 and t2 have the same sequence.

6. The method according to claim 1, wherein the sequences of both tags t3 and t2 are different from the sequence of tag t1.

7. The method according to claim 1, wherein F1^ has 3-30 nucleotides of the 5'-end partial F1 sequence.

8. The method according to claim 4, wherein F1^ has 3-30 nucleotides of the 5'-end partial F1 sequence.

9. The method according to claim 1, wherein F1^ has 40-90% of the 5'-end partial F1 sequence.

10. The method according to claim 4, wherein F1^ has 40-90% of the 5'-end partial F1 sequence.

11. The method according to claim 1, wherein F1, F2, R1, and R2 are gene-specific primers.

* * * * *

SEQUENCE LISTING

<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 1
aaaatgatga agtgacagtt ccag                                        24

<210> SEQ ID NO 2
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 2
cccatggaaa cagttcatgt atta                                        24

<210> SEQ ID NO 3
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 3
catggacttt tacaaaaccc atatc                                       25

<210> SEQ ID NO 4
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 4
agcccacttc attagtactg gaac                                        24

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
caacgatcgt cgaaattcgc                                             20

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 6
tacacgacgc tcttccgatc t                                           21

<210> SEQ ID NO 7
<211> LENGTH: 44
<212> TYPE: DNA
<213> ORGANISM: Artificial Sequence

```
<220> FEATURE:
<223> OTHER INFORMATION: synthetic oligonucleotide

<400> SEQUENCE: 7
caacgatcgt cgaaattcgc aaaatgatga agtgacagtt ccag                    44

<210> SEQ ID NO 8
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 8
tacacgacgc tcttccgatc tcccatggaa acagttcatg tatta                  45

<210> SEQ ID NO 9
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 9
caacgatcgt cgaaattcgc agcccacttc attagtactg gaac                   44

<210> SEQ ID NO 10
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 10
caacgatcgt cgaaattcgc aaaagcccac ttcattagta ctggaac                47

<210> SEQ ID NO 11
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 11
caacgatcgt cgaaattcgc aaaatgagcc cacttcatta gtactggaac             50

<210> SEQ ID NO 12
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 12
caacgatcgt cgaaattcgc aaaatgatga gcccacttca ttagtactgg aac         53

<210> SEQ ID NO 13
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 13
caacgatcgt cgaaattcgc aaaatgatga agagcccact tcattagtac tggaac      56
```

```
<210> SEQ ID NO 14
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 14
caacgatcgt cgaaattcgc aaaatgatga agtgaagccc acttcattag tactggaac      59

<210> SEQ ID NO 15
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 15
tacacgacgc tcttccgatc tcatggactt ttacaaaacc catatc                    46
```